United States Patent [19]

Boyd

[11] 4,211,745

[45] Jul. 8, 1980

[54] REFUSE CONTAINER SPRAYER

[76] Inventor: Leroy Boyd, 1932 Texas Ave., Lubbock, Tex. 79405

[21] Appl. No.: 699,534

[22] Filed: Jun. 24, 1976

[51] Int. Cl.$^2$ ........................ A61L 3/02; A61L 11/00; B08B 3/00; B65F 3/02

[52] U.S. Cl. ........................ 422/28; 134/102; 134/115 R; 134/152; 298/17 R; 414/408

[58] Field of Search ........................ 21/2, 61, 107; 134/22 R, 34, 37, 115 R, 152, 166 R, 102; 214/302, 303, 310; 298/17 R (U.S. only); 422/1, 28; 414/408

[56] References Cited

U.S. PATENT DOCUMENTS

| | | | |
|---|---|---|---|
| 3,188,238 | 6/1965 | Lyon | 134/102 X |
| 3,207,166 | 9/1965 | Wintzer | 298/17 RX |
| 3,282,273 | 11/1966 | Johnston et al. | 134/102 |
| 3,324,866 | 6/1967 | Davis | 214/302 X |
| 3,372,875 | 3/1968 | Torrey | 134/115 R X |
| 3,870,174 | 3/1975 | Brisson | 214/303 |
| 3,881,950 | 5/1975 | Pettit | 134/115 R |
| 3,901,255 | 8/1975 | Pettit | 134/115 R X |
| 3,923,174 | 12/1975 | Stragier | 214/302 X |

*Primary Examiner*—Joseph Scovronek
*Attorney, Agent, or Firm*—Wendell Coffee

[57] ABSTRACT

Spray nozzles are mounted on a refuse collection truck mechanically equipped to pick up refuse containers and dump the contents into the truck. The spray nozzles spray an insecticide, a deodorant, and a rust preventative lubricant into the container after it has been emptied, but before it is lowered to the ground.

2 Claims, 3 Drawing Figures

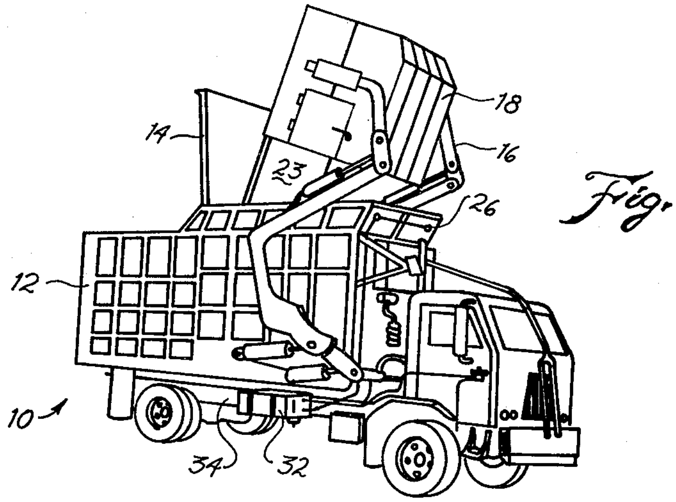
Fig. 1
Fig. 2
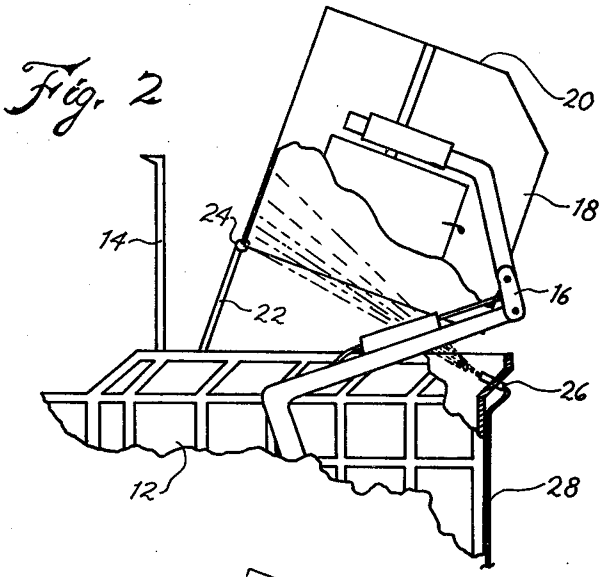
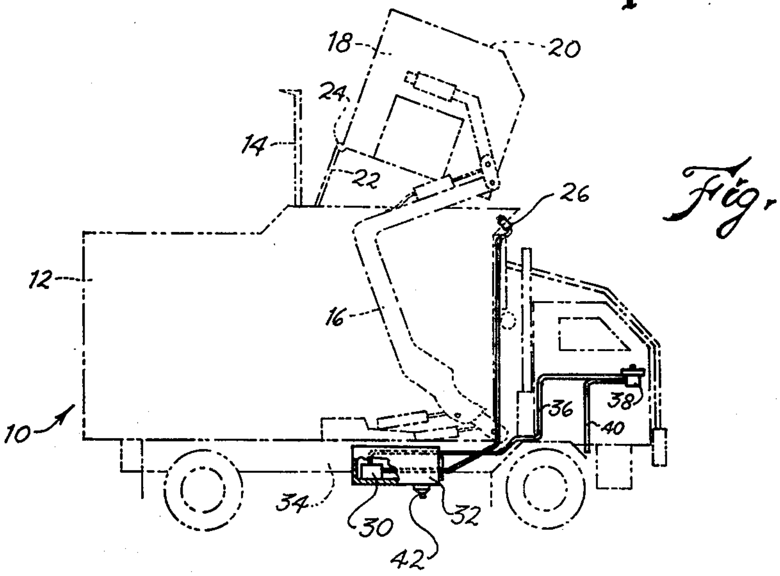
Fig. 3

REFUSE CONTAINER SPRAYER

CROSS-REFERENCE TO RELATED APPLICATIONS

None. However, by separate paper, it is requested that Disclosure Document #044683, filed Nov. 10, 1975, be retained.

BACKGROUND OF THE INVENTION

(1) Field of the Invention

This invention relates to solid waste disposal and more particularly to spraying refuse containers to prevent insects and rust, to deodorize, and to lubricate.

(2) Description of the Prior Art

Handling of domestic solid waste is greatly facilitated by placing the waste in large refuse containers. A common system is to have one large container for four households. Also, many restaurants and food establishments dispose of their waste in large containers. These large containers are emptied by a truck having arms thereon which lift the refuse container and invert it over a container on the truck body.

The trucks which empty the refuse containers are divided into three general categories: front loaders, side loaders and rear loaders.

The front loader truck approaches the refuse container head-on and arms extend from the truck to the container, lifting it over the cab of the truck to dump it into the container behind the cab. There the garbage may be packed, according to the design of the truck.

The side loader truck pulls along side the refuse container and arms extend from the side of the truck to engage the containers, dumping the contents into the truck from the side.

The rear loader truck necessitates that the refuse container, which has wheels under it, be rolled behind the collection truck where it is connected to a lift system, picked up, dumped into the truck and lowered to the ground.

Previous workers, such as LOVERCHECK, U.S. Pat. No. 3,547,577, have disclosed a system for sterilizing the refuse with gas after it has been dumped from the collection truck. However, LOVERCHECK does not sterilize the refuse container itself.

Likewise, JERNSTROM, U.S. Pat. No. 3,831,514, discloses deodorizing the household garbage compactor. However, there is no sterilization or deodorization of the front, side or rear loader refuse container.

DAVIS, U.S. Pat. No. 3,324,866, discloses a special truck which goes to the empty garbage container and cleans it. However, DAVIS does not collect garbage.

SUMMARY OF THE INVENTION

(1) New and Different Function

I have invented a system for spraying a refuse container with fluid after emptying. Of course, the sanitary engineers of any garbage collection system can use whatever spray they like, however, it is my opinion the best mode of operation is to spray them with an insecticide, deodorant and rust preventative lubricant. Insecticides sprayed into the can greatly reduce, if not completely remove, flies and insects from the refuse container. The deodorant improves the smell and the lubricant prevents squeaking hinges and reduces rust.

(2) Objects of this Invention

An object of this invention is to spray refuse containers.

Other objects are to reduce insects, odors, rust, and squeaks.

Further objects are to achieve the above with equipment that is sturdy, compact, durable, lightweight, simple, safe, efficient, ecologically compatible, energy conserving, versatile, and reliable, yet inexpensive and easy to manufacture, install, adjust, operate, and maintain.

Still further objects are to achieve the above with a method that is versatile, rapid, efficient, ecologically compatible, energy conserving, and inexpensive, and does not require highly skilled people to install, adjust, operate, and maintain.

The specific nature of the invention, as well as other objects, uses, and advantages thereof, will clearly appear from the following description and from the accompanying drawing, the different views of which are not to the same scale.

BRIEF DESCRIPTION OF THE DRAWING

FIG. 1 is a perspective view of a garbage handling system according to this invention showing the refuse container elevated and inverted over the truck wherein it is sprayed.

FIG. 2 is a side elevational view showing parts broken away to show the spray.

FIG. 3 is a side elevational view with the truck and refuse container shown in broken lines and the spray system schematically shown in full lines.

DESCRIPTION OF THE PREFERRED EMBODIMENT

Referring to the drawing, there may be seen represented truck 10. The truck is meant, except for the spray system, to represent a common truck, commercially on the market, for this service. As common with these trucks on the market, it will have refuse-containing body 12. The body will have upper door 14 and arms 16. Through numerous hydraulic controls, well known to the art and commonly available on the market, there will be a plurality of hydraulic cylinders so that refuse container 18 may be lifted, inverted and the contents thereof dumped into the truck body 12. After dumping, there may be a compaction of the garbage within the truck body 12. Arms with the hydraulic cylinder and the door opening for the truck body form an arm means for picking up the refuse container and inverting it over the body, thus dumping the contents of the can into the body.

Those skilled in the art will recognize that the refuse container 18 is illustrated in its inverted position and that normally the container sits on its bottom or nether side 20. Also, the container has lid 22 which is hinged by hinges 24 to the top back of the refuse container. As illustrated, when the container is inverted, the lid being inverted comes open and the contents are dumped into the truck body 12.

Workers in the art will recognize that the truck and refuse container as described to this point are conventional, commonly available on the market. Also, those skilled in the art will recognize that the verbal description as given to this point is equally applicable to a front-loading refuse collection truck as well as side-loading and rear loading trucks, although the drawing illustrates a front-loading refuse truck.

To this front-loading system, I add spray nozzles 26 upon the truck at the forward, upper portion of the refuse-containing truck body. These nozzles are connected by tube or hose 28 to metered hydro-pneumatic or hydraulic pump 30 located within reservoir 32 attached to chassis 34 of the truck 10. The pump 30 is connected by tube or hose 36 to actuation valve 38 located conveniently in the truck cab. Supply hose 40 extends from a source of pneumatic or hydraulic pressure on the truck. It is common and conventional for trucks of this type to have a supply of pneumatic or hydraulic pressure. The hose 40 is a source of fluid under pressure to the system.

Fluid filter 42 is attached to the reservoir.

OPERATION

The operator in the truck 10 approaches a refuse container 18, connects the arms to the container, lifts and inverts it, thus dumping the contents of the container 18 into the refuse container 12 on the truck. Then with the container inverted and the container lid 22 open, the operator actuates the valve 38 which sends pressure to the pump 30 which sends a pulse of fluid under higher pressure. The fluid has been filtered by the filter 42 through the hose 28 to the nozzles 26, thus projecting a spray of a measured amount of fluid into the inverted refuse container 18. The spray is directed inside and to the nether side of the hinges 24. In the present orientation of the container 18, this will be immediately above the hinges 24. Therefore, some of the spray will run down to the hinges, thus lubricating them.

Immediately after spraying the container, the operator will return the container to its original position with the nether side down on the ground. In this position, the lid 22 will close and the fluid which has been sprayed into the container will run down into the bottom of the container. Inasmuch as most insecticides are volatile, the fumes from the insecticide will fill the container, effectively controlling insects in and around the refuse container 18.

As stated previously, those sanitation engineers can choose the exact contents of the fluid to be used. As stated before, I prefer to use an insecticide to kill and control flies and other insects. In addition, I prefer to use a deodorizer to reduce odors to the extent possible and to include a lubricant and rust preventer to lubricate the hinges of the refuse container against wear, prevent the hinges from squeaking, and prevent rust to the extent possible within the refuse container. The lubricant also lubricates the pump 30.

Also, those skilled in this art will understand how to provide an actuation valve 38, how to connect the valve to the source of supply of pressure on the truck and how to make this actuation valve operate a pump to pump a measured spray.

As a matter of design preference, I prefer to use about one-fourth liter of spray each time the actuation valve 38 is used. Others skilled in the art may prefer to spray as long as the valve is controlled and allow the operator to spray more or less fluid according to how long he presses the valve. Some may prefer to have the spray automatically activated from the position of the arms 16, or time in the cycle, which automation is well within the skill of those in the art. My preference is to have the spray pressure about eight times the air pressure, but those skilled in hydraulic arts will be able to determine for themselves at their own installations the spray pressures they desire.

Also, the system is equally applicable to side-load or rear-load systems with the nozzles properly positioned.

As an aid to correlating the terms of the claims to the exemplary drawing, the following catalog of elements is provided:

10 truck
12 body
14 door
16 arms
18 refuse container
20 nether side
22 lid
24 hinges
26 nozzles
28 hose
30 metered pump
32 reservoir
34 chassis
36 pressure hose
38 actuation valve
40 supply
42 fluid filter The embodiment shown and described above is only exemplary. I do not claim to have invented all the parts, elements or steps described. Various modifications can be made in the construction, material, arrangement, and operation, and still be within the scope of my invention. The limits of the invention and the bounds of the patent protection are measured by and defined in the following claims. The restrictive description and drawing of the specific example above do not point out what an infringement of this patent would be, but are to enable the reader to make and use the invention.

I claim as my invention:

1. In a solid refuse gathering system including
a. a refuse container, and
b. a truck having thereon
(i) a refuse containing body and
(ii) arm means for picking up the refuse container and inverting it over the body, thus dumping the contents of the container into the body,
c. said container having a hinged lid thereon;
d. the improved method of spraying the container comprising the steps of:
e. spraying the interior of the container while it is inverted over the truck after the contents of the container have been dumped,
f. timing the spraying operation to coincide with a period of time when the lid of the container is open because of the inverted position of the container,
g. the spray contains a rust preventive lubricant for the hinge on the lid of the container.

2. The invention as defined in claim 1 further comprising the spray contains an insecticide.

* * * * *